US012102299B2

(12) United States Patent
Awau

(10) Patent No.: US 12,102,299 B2
(45) Date of Patent: Oct. 1, 2024

(54) ENDOSCOPE REPROCESSOR

(71) Applicant: OLYMPUS CORPORATION, Tokyo (JP)

(72) Inventor: Yumiko Awau, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 1037 days.

(21) Appl. No.: 17/038,743

(22) Filed: Sep. 30, 2020

(65) Prior Publication Data
US 2021/0076923 A1    Mar. 18, 2021

Related U.S. Application Data

(63) Continuation of application No. PCT/JP2019/014968, filed on Apr. 4, 2019.

(30) Foreign Application Priority Data

Apr. 17, 2018    (JP) ................. 2018-079080

(51) Int. Cl.
*A61B 1/12* (2006.01)
*A61B 1/00* (2006.01)
*A61B 90/70* (2016.01)

(52) U.S. Cl.
CPC .......... *A61B 1/123* (2013.01); *A61B 1/00011* (2013.01); *A61B 2090/701* (2016.02)

(58) Field of Classification Search
CPC .................................................... A61B 1/123
See application file for complete search history.

(56) References Cited

U.S. PATENT DOCUMENTS

| 2007/0107152 A1* | 5/2007 | Noguchi | ............... A61B 1/125 |
| | | | 15/104.095 |
| 2017/0087604 A1* | 3/2017 | Kosugi | ................. G02B 23/24 |

FOREIGN PATENT DOCUMENTS

| DE | 102013202540 A1 * | 8/2014 | ............... A61L 2/24 |
| EP | 3 162 277 A1 | 5/2017 | |
| JP | 2002-272684 A | 9/2002 | |
| JP | 2009-039207 A | 2/2009 | |
| JP | 2009-165506 A | 7/2009 | |
| JP | 2013-135935 A | 7/2013 | |
| WO | 2017/038132 A1 | 3/2017 | |

OTHER PUBLICATIONS

DE102013202540A1 Machine Translation (Year: 2014).*
International Search Report dated Jun. 18, 2019 received in PCT/JP2019/014968.

* cited by examiner

*Primary Examiner* — Spencer E. Bell
(74) *Attorney, Agent, or Firm* — Scully, Scott, Murphy & Presser, P.C.

(57) ABSTRACT

An endoscope reprocessor includes: a treatment tank; a transmission panel made of a transmitting material that allows an observation wave to transmit through the transmitting material, the transmission panel being disposed such that the observation wave is allowed to transmit from a reprocessor outer surface to an inside of the treatment tank; and at least one terminal holding member disposed on the reprocessor outer surface, and configured to hold an observation terminal at a position that allows the observation terminal to observe the inside of the treatment tank through the transmission panel, the observation terminal including a receiver that receives the observation wave.

13 Claims, 16 Drawing Sheets

ENDOSCOPE REPROCESSOR

CROSS REFERENCE TO RELATED APPLICATION

This application is a continuation application of PCT/JP2019/014968 filed on Apr. 4, 2019 and claims benefit of Japanese Application No. 2018-079080 filed in Japan on Apr. 17, 2018, the entire contents of which are incorporated herein by this reference.

BACKGROUND OF THE INVENTION

1. Field of the Invention

The present invention relates to an endoscope reprocessor.

2. Description of the Related Art

Conventionally, endoscope reprocessors have been used that perform reprocessing, such as cleaning and disinfecting, on an endoscope used on a subject. To properly perform the reprocessing, there is a demand for the endoscope reprocessor to adopt a technique to determine whether or not the endoscope reprocessor is being used with an endoscope being appropriately disposed.

For example, Japanese Patent Application Laid-Open Publication No. 2002-272684 discloses an endoscope cleaning device where the inside of a cleaning tank is irradiated with ultrasound to detect ultrasound reflection information and, thereafter, it is possible to determine whether or not an endoscope is appropriately disposed based on the ultrasound reflection information and RFID information.

SUMMARY OF THE INVENTION

An aspect of the present invention is directed to an endoscope reprocessor including: a transmission panel made of a transmitting material that allows an observation wave to transmit through the transmitting material, the transmission panel being disposed such that the observation wave is allowed to transmit from a reprocessor outer surface to an inside of a treatment tank; and at least one terminal holding member disposed on the reprocessor outer surface, and configured to hold an observation terminal at a position that allows the observation terminal to observe the inside of the treatment tank through the transmission panel, the observation terminal including a receiver that receives the observation wave.

DETAILED DESCRIPTION OF THE PREFERRED EMBODIMENTS

Hereinafter, embodiments of the present invention will be described with reference to drawings.

First Embodiment

Figure 1:
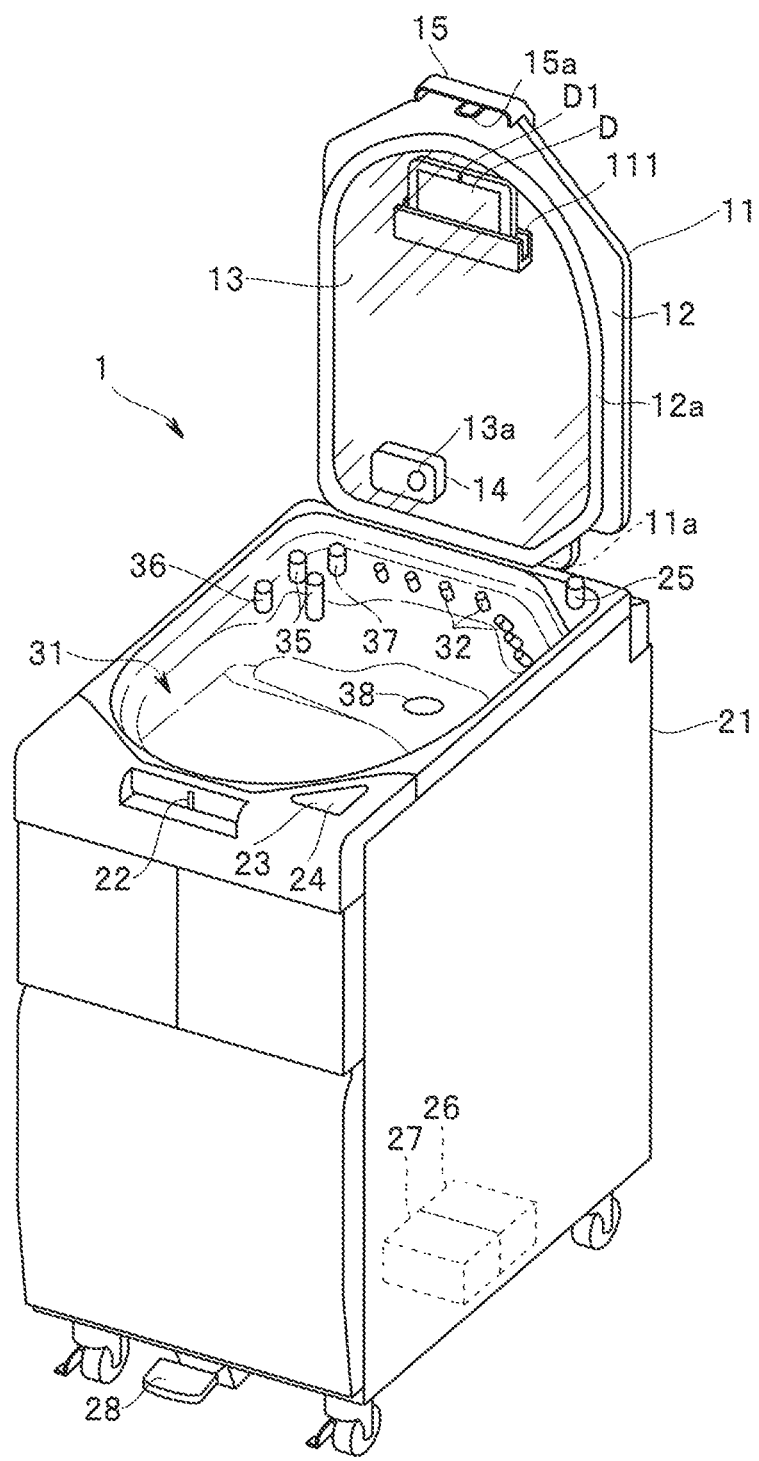
FIG. 1 is a perspective view of an endoscope reprocessor according to a first embodiment of the present invention.
Figure 2:
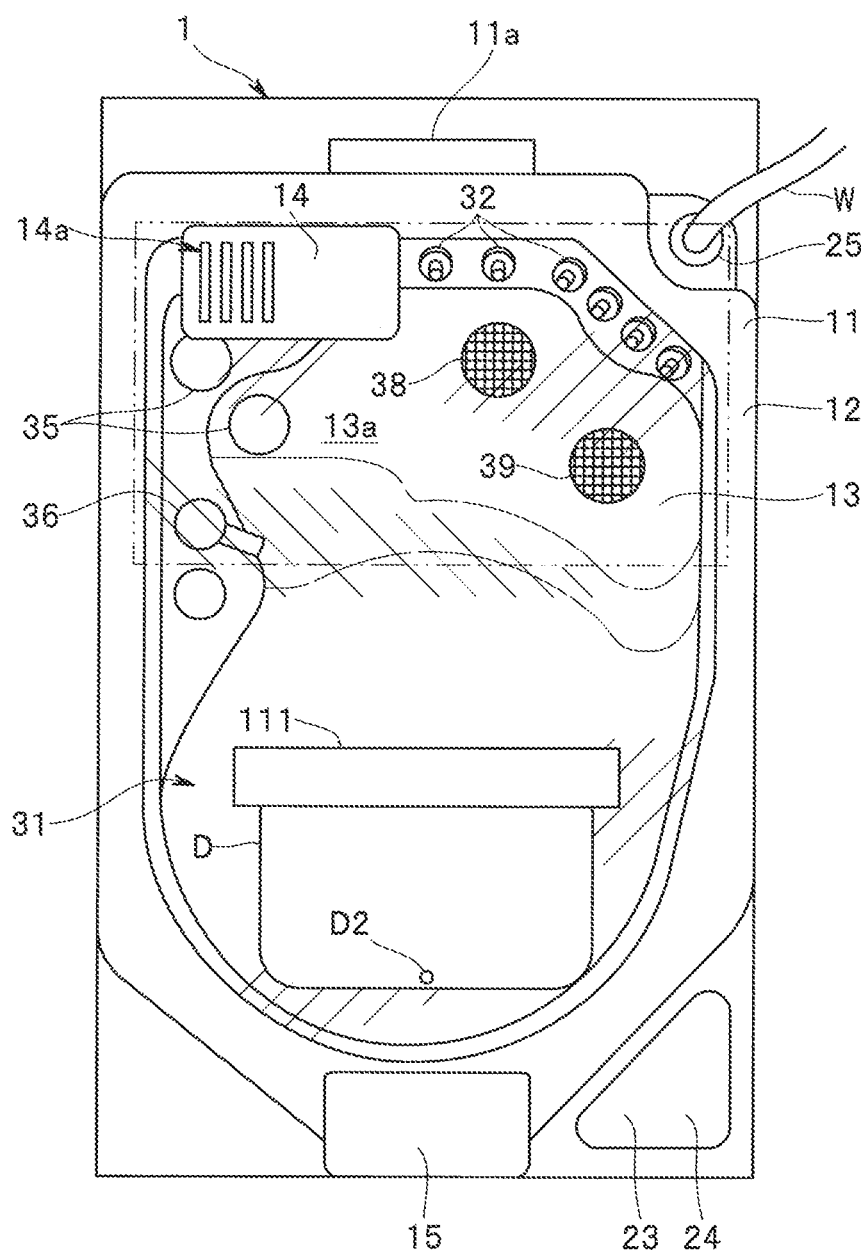
FIG. 2 is a top plan view of the endoscope reprocessor according to the first embodiment of the present invention.

FIG. 1 is a perspective view of an endoscope reprocessor 1 according to a first embodiment of the present invention. FIG. 2 is a top plan view of the endoscope reprocessor 1 according to the first embodiment of the present invention.

Figure 3:
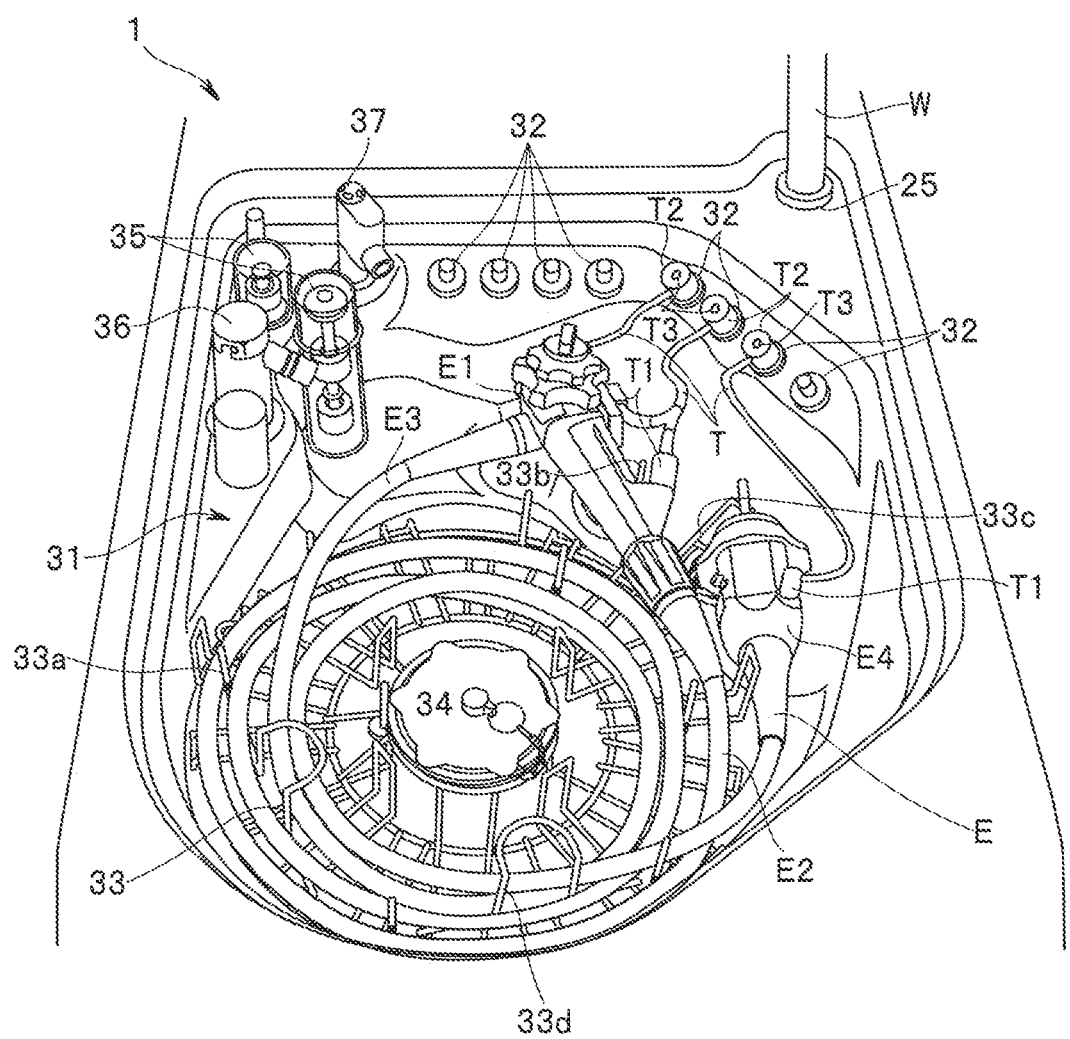
FIG. 3 is an explanatory view for describing a state where an endoscope is disposed in a treatment tank of the endoscope reprocessor according to the first embodiment of the present invention.

FIG. 3 is an explanatory view for describing a state where an endoscope E is disposed in a treatment tank 31 of the endoscope reprocessor 1 according to the first embodiment of the present invention.

The endoscope reprocessor 1 is a device that performs reprocessing on the contaminated endoscope E, and components or accessories of the endoscope E, or the like. In the embodiment, reprocessing is not particularly limited, and may be any one of rinsing with water, cleaning to remove stains caused by organic matter or the like, disinfecting to make predetermined microorganisms inactive, sterilizing to eliminate or kill all microorganisms, or a combination of these. Further, the endoscope reprocessor 1 may be used for performing reprocessing on tubular medical equipment, such as dilators or endoscope sheaths.

In the description made hereinafter, a downward direction indicates a gravity direction, an upward direction indicates a direction opposite to the gravity direction, and a high or a low indicates a height relationship along the gravity direction.

In the present embodiment, the endoscope reprocessor 1 includes a top cover 11, a reprocessor body 21, and a terminal holding member 111. The top cover 11 has a cover panel 13, which acts as a transmission panel. The terminal holding member 111 is provided to the top cover 11. The terminal holding member 111 holds an observation terminal D that receives visible light as an observation wave.

The top cover 11 is disposed such that the back surface of the top cover 11 faces the treatment tank 31 of the reprocessor body 21. The top cover 11 opens and closes the treatment tank 31 by rotating about a hinge 11a. In other words, one end of the top cover 11 is connected to the reprocessor body 21 by the hinge 11a, and the other end of the top cover 11 rotates about the one end of the top cover 11. When the top cover 11 is brought into a closed state, the top cover 11 covers the treatment tank 31. The top cover 11 includes a cover frame 12, the cover panel 13 being the transmission panel, a gas filter 14, and a finger hooking portion 15.

The cover frame 12 is made of a material, such as metal or a resin, and is provided to surround a periphery portion of the top cover 11. The cover frame 12 has a packing 12a on a back surface of the cover frame 12, and the packing 12a is provided to surround and extend along an upper edge portion of the treatment tank 31. When the top cover 11 is brought into the closed state, the packing 12a is brought into close contact with the upper edge portion of the treatment tank 31.

The cover panel 13 has light transmitting properties. An example of a transmitting material for forming the cover panel 13 may be a resin or ceramic. A resin may be polycarbonate having chemical resistance and visible light transmitting properties. The cover panel 13 is provided inside the cover frame 12. The configuration of the cover panel 13 is not particularly limited. The cover panel 13 may have a cover discharge port 13a at a portion close to the one end of the cover panel 13 and bulging into a dome shape.

The gas filter 14 is formed of a filter medium accommodating container and a filter medium. The filter medium accommodating container is made of a material, such as a resin. The filter medium is accommodated in the filter medium accommodating container. The gas filter 14 is detachably attached to the cover discharge port 13a. The gas filter 14 has a filter discharge port 14a at an upper portion of the gas filter 14 (FIG. 2). The gas filter 14 takes in a gas in the treatment tank 31 through the cover discharge port 13a, and discharges, through the filter discharge port 14a, the gas subjected to filtering for deodorizing or the like.

The finger hooking portion 15 is made of a material, such as metal or a resin. The finger hooking portion 15 is continuously formed with the other end side of the cover frame 12 to allow a user to hook his/her finger on the finger hooking portion 15. A fastener 15a is provided inside the finger hooking portion 15.

The reprocessor body 21 includes a locking unit 22, a display panel 23, an operation unit 24, a water supply hose connection port 25, a communication unit 26, a control unit 27 and the treatment tank 31.

The locking unit 22 is provided on the other end side of an upper portion of the reprocessor body 21. Under the control of the control unit 27, the locking unit 22 engages with the fastener 15a or releases the engagement with the fastener 15a. When the locking unit 22 engages with the fastener 15a, the top cover 11 is locked in the closed state. It may be configured such that the locking unit 22 is linked with a foot panel 28 to allow the engagement of the locking unit 22 with the fastener 15a to be released in response to an operation of the foot panel.

The display panel 23 is provided to a corner portion on the other end side of the upper portion of the reprocessor body 21. The display panel 23 is configured to display various notifications to a user under the control of the control unit 27.

The operation unit 24 has an instruction input button to input various instructions to the endoscope reprocessor 1.

The water supply hose connection port 25 is connected with a water faucet via a water supply tube W.

The communication unit 26 is connected with the control unit 27, and is configured such that the communication unit 26 can communicate with the observation terminal D by wired or wireless communication under the control of the control unit 27. It may be configured such that the communication unit 26 can communicate with an external device via a network.

The control unit 27 controls respective units in the endoscope reprocessor 1. The control unit 27 includes a processor and a memory, and can execute various programs stored in the memory. A function of the control unit 27 is achieved by reading and executing the program stored in the memory.

The control unit 27 is connected with the observation terminal D via the communication unit 26. When the control unit 27 receives an input of a determination result indicating an abnormality from the observation terminal D, the control unit 27 notifies a user of an abnormality. An abnormality notification may be a warning displayed on the display panel 23, or an output of a warning sound from a speaker not shown in the drawing. Further, When the control unit 27 receives the input of the determination result indicating an abnormality from the observation terminal D, the control unit 27 may perform a control to stop reprocessing.

As shown in FIG. 3, the treatment tank 31 is provided to the upper portion of the reprocessor body 21. As shown in FIG. 3, when the top cover 11 is brought into an open state, the treatment tank 31 is exposed to the outside. The treatment tank 31 has a recessed shape to accommodate the endoscope E that performs reprocessing and to store a liquid, such as a cleaning solution, a disinfecting liquid or a rinsing liquid. The treatment tank 31 has air/water feeding connectors 32, a holding net 33, a cleaning casing 34, water level gauges 35, a medicinal solution nozzle 36, a water supply circulation nozzle 37, a circulation port 38, and a liquid discharge port 39.

In the treatment tank 31, cleaning tubes T connect the reprocessor body 21 and the endoscope E with each other. Each cleaning tube T includes an endoscope-side connector T1 connected with the endoscope E, and a processor-side connector T2 connected with the reprocessor body 21. The reprocessor-side connector T2 has an ejection port T3 from which liquid ejects in a liquid passing state.

The endoscope E includes, for example, an endoscope operation portion E1, an insertion portion E2, a universal cord E3, and a scope connector E4. The insertion portion E2 has an elongated shape that extends from the endoscope operation portion E1 toward a distal end side of the endoscope E. The universal cord E3 extends from the endoscope operation portion E1. The scope connector E4 is caused to extend from a distal end side of the universal cord E3. The endoscope-side connectors T1 are connected to the endoscope operation portion E1 and the scope connector E4.

The air/water feeding connectors 32 are provided to a wall portion of the treatment tank 31. The reprocessor-side connectors T2 are connected to the air/water feeding connectors 32. Eight air/water feeding connectors 32 are shown in FIG. 3. However, the number of air/water feeding connectors 32 is not limited to eight. The air/water feeding connectors 32 are connected with the circulation port 38 through conduits. When the control unit 27 drives a circulation pump, the air/water feeding connectors 32 takes in liquid through the circulation port 38, and feed the liquid to the endoscope E. Further, when the control unit 27 drives an air compressor, the air/water feeding connectors 32 takes in air from the atmosphere, and feed the air to the endoscope E.

The holding net 33 is made of a material, such as metal or a resin, and is attached to a bottom portion of the treatment tank 31. The holding net 33 includes an index pin 33a, an operation portion receiving portion 33b, a scope connector receiving portion 33c, and a hook 33d. The index pin 33a has a mark indicating a height of disinfecting liquid level. The operation portion receiving portion 33b is provided for disposing the endoscope operation portion E1. The scope connector receiving portion 33c is provided for disposing the scope connector E4. The hook 33d is provided for hooking the insertion portion E2 and the universal cord E3. A user disposes the endoscope operation portion E1 to the operation portion receiving portion 33b, disposes the scope connector E4 to the scope connector receiving portion 33c, and winds the insertion portion E2 and the universal cord E3 such that the insertion portion E2 and the universal cord E3 pass on the inside of the hook 33d. The user causes the endoscope E to be held by the holding net 33 such that the endoscope E is disposed below the mark on the index pin 33a to prevent the endoscope E from exceeding the disinfecting liquid level.

The cleaning casing 34 is attached to a center portion of the holding net 33. Accessories removed from the endoscope E, such as an air/water feeding button, a suction button, and a cap, are accommodated in the cleaning casing 34. A lower portion of the cleaning casing 34 is connected with a bottom portion connector provided to a bottom portion of the reprocessor body 21. Under the control of the control unit 27, air or water is fed to the cleaning casing 34 from the bottom portion connector. The accessories are not particularly limited. Examples of the accessories are the suction button, the air/water feeding button, and a distal end cover that covers a distal end portion of the endoscope E, which are mounted on the endoscope E during the use and removed from the endoscope E at the time of performing reprocessing.

The water level gauges 35 measure a level of liquid in the cleaning tank, and outputs the measurement result to the control unit 27.

The medicinal solution nozzle 36 is provided to a terrace portion provided at a position one step higher than other portions of a periphery portion in the treatment tank 31. The medicinal solution nozzle 36 is connected with a medicinal solution tank in the reprocessor body 21. When the control unit 27 drives a medicinal solution pump, the medicinal solution nozzle 36 discharges medicinal solution in the medicinal solution tank into the treatment tank 31.

The water supply circulation nozzle 37 is provided to the terrace portion. The water supply circulation nozzle 37 is connected with the circulation port 38 through a conduit. When the control unit 27 drives the circulation pump, the water supply circulation nozzle 37 takes in liquid through the circulation port 38, and discharges the liquid into the treatment tank 31. Under the control of the control unit 27, the water supply circulation nozzle 37 also discharges, to the treatment tank 31, water supplied through the water supply tube W via the water supply hose connection port 25.

Each of the circulation port 38 and the liquid discharge port 39 is formed on the bottom portion of the treatment tank 31, and a mesh filter is mounted on each of the circulation port 38 and the liquid discharge port 39 (FIG. 2). Liquid is taken into the treatment tank 31 through the circulation port 38. The liquid discharge port 39 is connected with external liquid discharge means, and the liquid in the treatment tank 31 is discharged to the outside through the liquid discharge port 39. Further, the liquid discharge port 39 can be connected with the medicinal solution tank under the control of the control unit 27. In the case where the liquid discharge port 39 is connected with the medicinal solution tank, medicinal solution used in the treatment tank 31 is recovered into the medicinal solution tank.

An example of medicinal solution used in the endoscope reprocessor 1 may be peracetic acid solution. Peracetic acid solution is prepared in the endoscope reprocessor 1 at a predetermined concentration in such a manner that a stock solution is diluted with water supplied through the water supply tube W. The medicinal solution is stored in the medicinal solution tank, and is discharged to the treatment tank 31 from the medicinal solution nozzle 36 at the time of disinfecting the endoscope E. After the medicinal solution is used for disinfecting the endoscope E, the medicinal solution is recovered into the medicinal solution tank so as to be used in the next reprocessing. A concentration of medicinal solution decreases with the number of use days and the number of use times. The medicinal solution may be prepared by the endoscope reprocessor 1.

The terminal holding member 111 is made of a material, such as metal or a resin, and is provided to a front surface side on a side opposite to the back surface side of the top cover 11 (FIG. 2). The terminal holding member 111 is configured such that the terminal holding member 111 can hold the observation terminal D at a position that allows the observation terminal D to observe the inside of the treatment tank 31 through the cover panel 13. In other words, the terminal holding member 111 is disposed on an outer surface of the top cover 11.

Figure 4:
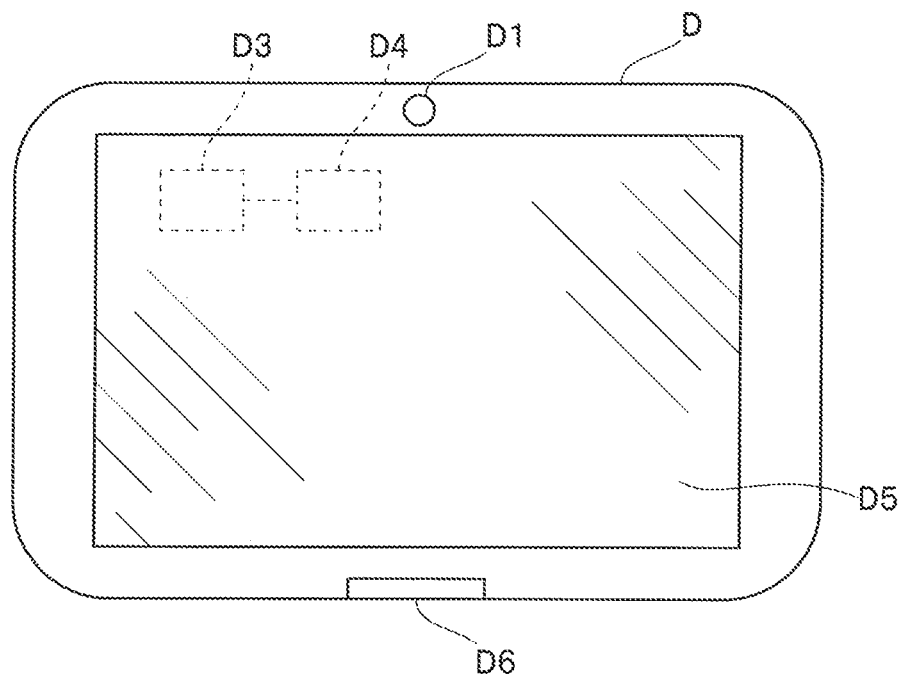
FIG. 4 is a front view of an observation terminal of the endoscope reprocessor according to the first embodiment of the present invention.
Figure 5:
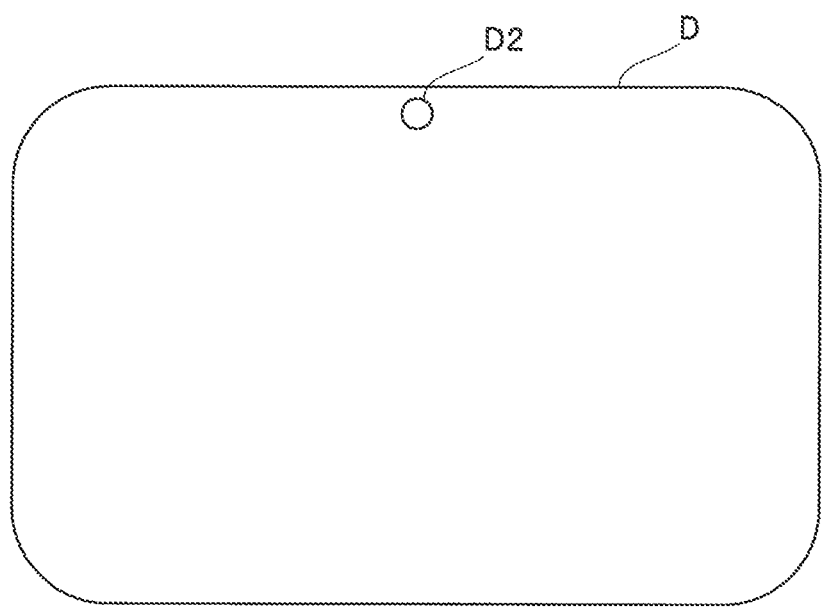
FIG. 5 is a back view of the observation terminal of the endoscope reprocessor according to the first embodiment of the present invention.

FIG. 4 is a front view of the observation terminal D of the endoscope reprocessor 1 according to the first embodiment of the present invention. FIG. 5 is a back view of the observation terminal D of the endoscope reprocessor 1 according to the first embodiment of the present invention.

As shown in FIG. 4 and FIG. 5, the observation terminal D is a portable information terminal of a tablet type, for example. The observation terminal D includes cameras D1, D2, a control unit D3, a communication unit D4, a display panel D5 and an external connection connector D6.

The camera D1 is provided to a front surface of the observation terminal D. The camera D2 is provided to a rear surface of the observation terminal D. The camera D1, D2 includes an image pickup device formed of a CMOS, a CCD or the like, picks up an image of the outside, and outputs the picked-up image to the control unit D3. The camera D1, D2 may include a wide angle lens. The wide angle lens may be fixed to the observation terminal D, or may be detachably mounted on the observation terminal D.

In other words, the camera D1, which acts as a receiver, receives visible light reflected in the treatment tank 31 and transmitting through the cover panel 13.

The control unit D3 includes a processor and a memory, and controls actions of respective units in the observation terminal D. The control unit D3 detects use state information from a picked-up image or a movie. Examples of the use state information may be a disposition state of the endoscope E, a connection state between the endoscope E and the reprocessor body 21, a waterproof state of the endoscope E, a mounting state of the mesh filter, a liquid passing state of the conduit, a driving state of the pump, and a concentration state of medicinal solution. The use state information may be all of or some of these states, or may be use state information indicating other use state.

Further, the control unit D3 determines based on the detection result whether the use state information is normal or abnormal, and outputs the determination result.

The communication unit D4 communicates with the communication unit 26, and outputs the determination result to the control unit 27.

The display panel D5 can display various types of information on a display panel under the control of the control unit D3. The display panel D5 may display the determination result. In the display panel D5, a touch panel is made to overlap so that it is possible to input various instructions by touch operation.

The external connection connector D6 is electrically connected with an external device.

In other words, the endoscope reprocessor 1 includes the top cover 11 and at least one terminal holding member 111. The top cover 11 is made of a material that allows light to transmit through the material, that is, a material having light transmitting properties, and the top cover 11 is disposed such that light is allowed to transmit from a reprocessor outer surface to the inside of the treatment tank 31. The terminal holding member 111 is disposed on the reprocessor outer surface, and holds the observation terminal D at a position that allows the observation terminal D to observe the inside of the treatment tank 31 through the cover panel 13, the observation terminal D including the cameras D1, D2 that receive light. The observation terminal D includes the camera D1 that receives light, and the observation terminal D observes the inside of the treatment tank 31 using the light.

(Detection and Determination of Use State Information)

Subsequently, detection and determination of the use state information will be described.

A user causes the endoscope E to be held by the holding net 33, and connects the endoscope E and the reprocessor body 21 by the cleaning tubes T, and then brings the top cover 11 into the closed state.

In the observation terminal D, the camera D1 picks up an image of the inside of the treatment tank 31, and outputs the picked-up image to the control unit D3.

The control unit D3 detects use state information.

For example, the control unit D3 detects, based on the picked-up image, a disposition state of the endoscope E depending on respective positions of the endoscope operation portion E1, the insertion portion E2, the universal cord E3, and the scope connector E4.

For example, the control unit D3 detects and determines, based on the picked-up image, a connection state between the endoscope E and the reprocessor body 21, such as a kind of the cleaning tube T, a mounting state of the endoscope-side connector T1 on the endoscope E, a mounting state of the reprocessor-side connector T2 on each air/water feeding connector 32, removal of the cleaning tube T not in use, and bending of the cleaning tube T.

For example, the control unit D3 detects, based on the picked-up image, a waterproof state of the endoscope E, such as whether or not the waterproof cap is mounted on the scope connector E4.

For example, the control unit D3 detects, based on the picked-up image, a mounting state of the mesh filter on each of the circulation port 38 and the liquid discharge port 39, such as mounting of the mesh filter, and whether or not the mesh filter is clogged.

Figure 6:
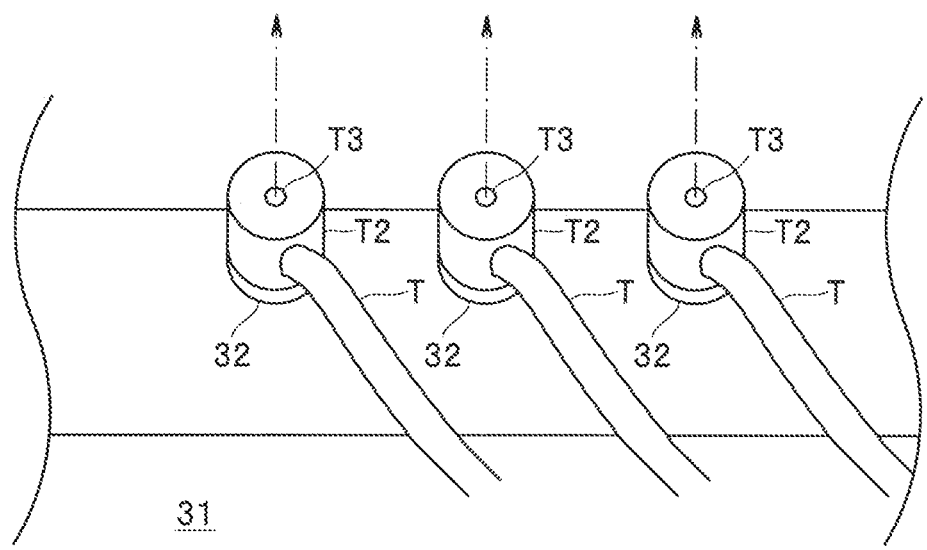
FIG. 6 is an explanatory view for describing an example of detecting a liquid passing state of conduits of the endoscope reprocessor according to the first embodiment of the present invention.

FIG. 6 is an explanatory view for describing an example of detecting a liquid passing state of the conduits of the endoscope reprocessor 1 according to the first embodiment of the present invention.

For example, when the control unit 27 drives the reprocessor body 21 to feed liquid to the air/water feeding connectors 32, a portion of the liquid is ejected from the ejection ports T3 (dashed-and-dotted lines in FIG. 6). The camera D1 picks up an image of the liquid ejected from the ejection ports T3, and outputs the picked-up image to the control unit D3. The control unit D3 detects, based on the picked-up image, a liquid passing state of the conduits depending on whether or not the ejected liquid is impinging on the back surface of the top cover 11.

For example, the control unit 27 drives the reprocessor body 21 to cause the liquid taken into the reprocessor body 21 from the circulation port 38 to be discharged from the water supply circulation nozzle 37. The camera D1 picks up an image of the water supply circulation nozzle 37, and outputs the picked-up image to the control unit D3. The control unit D3 detects, based on the picked-up image, a driving state of the pump depending on whether or not liquid is being discharged from the water supply circulation nozzle 37.

Figure 7:
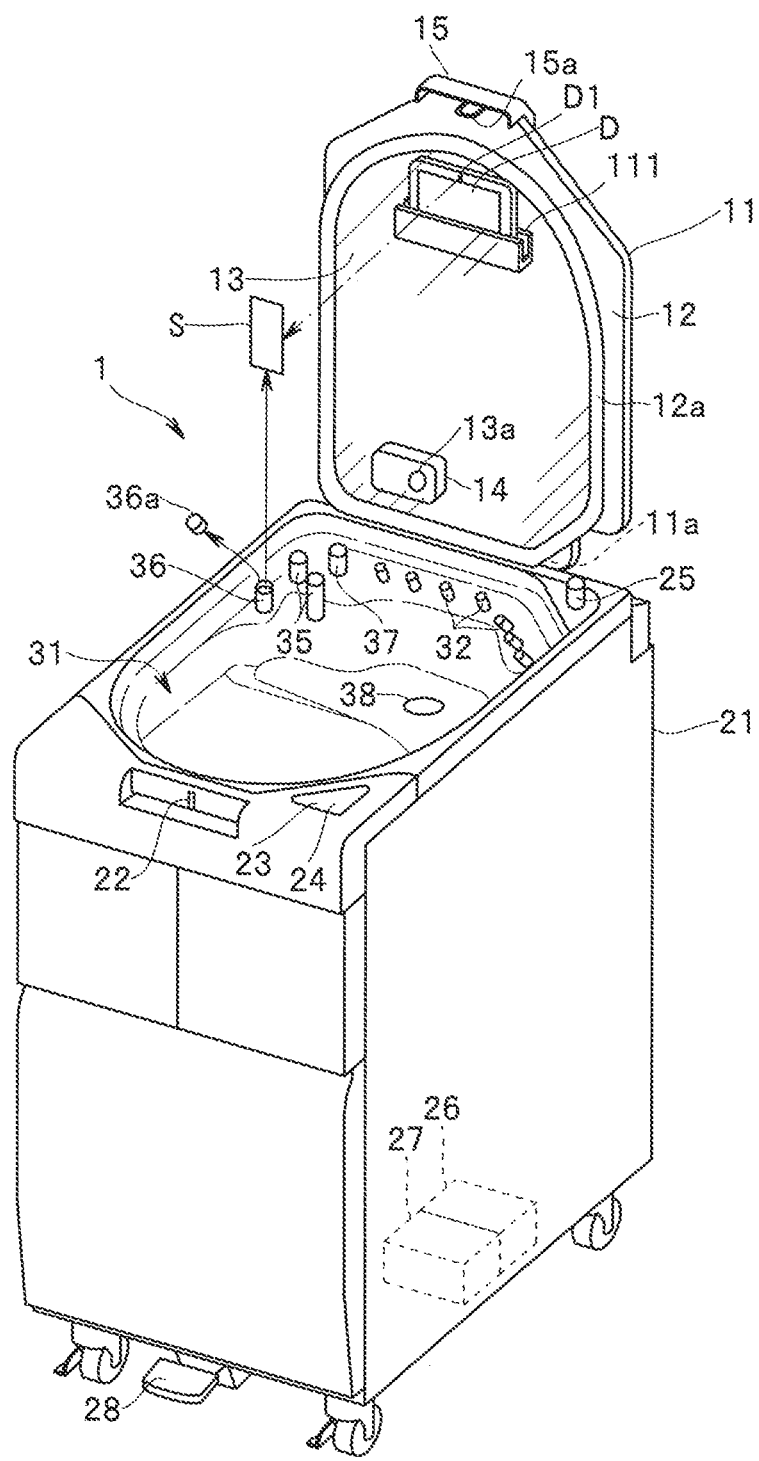
FIG. 7 is an explanatory view for describing an example of detecting a concentration state of medicinal solution in the endoscope reprocessor according to the first embodiment of the present invention.
Figure 8:
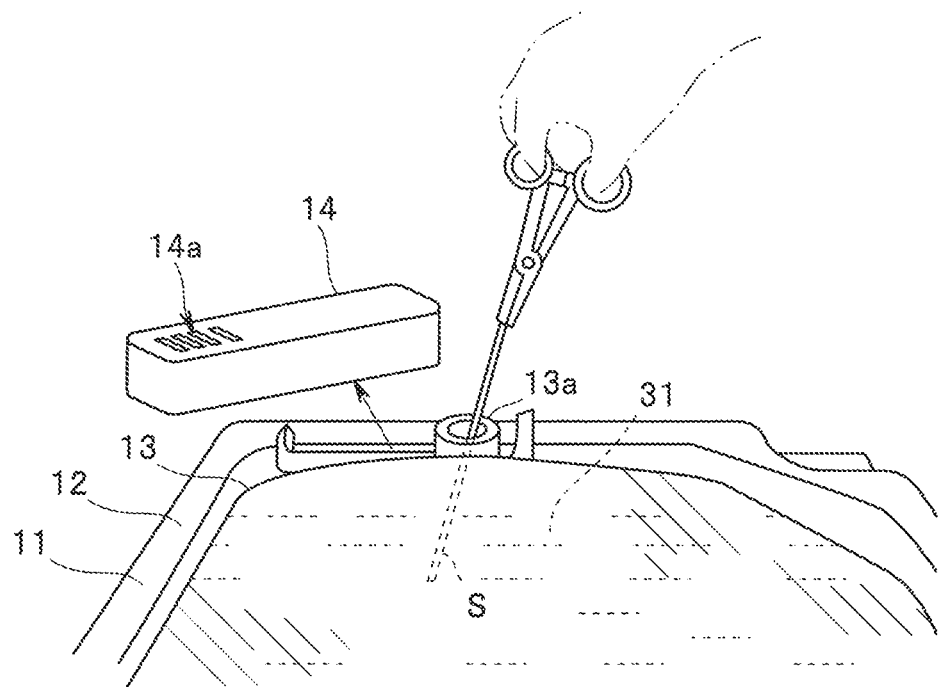
FIG. 8 is an explanatory view for describing an example of detecting a concentration state of the medicinal solution in the endoscope reprocessor according to the first embodiment of the present invention.

Each of FIG. 7 and FIG. 8 is an explanatory view for describing an example of detecting a concentration state of medicinal solution in the endoscope reprocessor 1 according to the first embodiment of the present invention.

For example, as shown in FIG. 7, a user opens the top cover 11, and removes a cap 36a of the medicinal solution nozzle 36 to cause a test paper S to be immersed in the liquid in the medicinal solution nozzle 36 for a predetermined time period. After the test paper S is immersed in the liquid for the predetermined time period, the user removes excess liquid from the test paper S in a liquid removing operation, and causes the camera D1 to pick up an image of the test paper S. The camera D1 picks up the image of the test paper S, and outputs the picked-up image to the control unit D3. The control unit D3 detects, based on the picked-up image, a concentration state of medicinal solution depending on the degree of color change in the test paper S.

At this point of operation, the observation terminal D may give a user support for a test method, such as an immersion time period of the test paper S or a liquid removal time period. Examples of a support method may include a method of displaying the immersion time period or the liquid removal time period on the display panel D5 of the observation terminal D, a method of displaying a count timer for counting from the start to the end of the immersion time period or the liquid removal time period on the display panel D5, a method that the observation terminal D informs the immersion time period or the liquid removal time period by voice, and a method that the observation terminal D counts from the start to the end of the immersion time period or the liquid removal time period by voice.

The user may cause medicinal solution to adhere to the test paper S using a technique disclosed in WO2013/011724. Alternatively, as shown in FIG. 8, the user may remove the gas filter 14 to cause the test paper S to be immersed in medicinal solution in the treatment tank 31 from the filter discharge port 14a. Alternatively, the user may insert the test paper S from an opening of the medicinal solution tank to immerse the test paper S into medicinal solution. Alternatively, although not shown in the drawing, the user may collect medicinal solution into a container from a drain port, and may measure a concentration by inserting the test paper S into the container.

The control unit D3 compares the detection result and reference information stored in advance in the memory to determine whether the detection result falls within a normal range or falls outside the normal range, that is, in an abnormal range. Then, the control unit D3 outputs the determination result to the control unit 27 via the communication units D4, 26.

When the control unit 27 receives an input of the determination result indicating an abnormality, the control unit 27 displays a warning on the display panel 23 to notify a user of an abnormality.

According to the embodiment, the endoscope reprocessor 1 can be more easily equipped with the observation terminal D, which determines whether or not the endoscope reprocessor 1 is being used in an appropriate use state.

Modification 1 of First Embodiment

A terminal holding member 211 may have a substantially U shape in cross section continuing in a length direction, for example.

Figure 9:
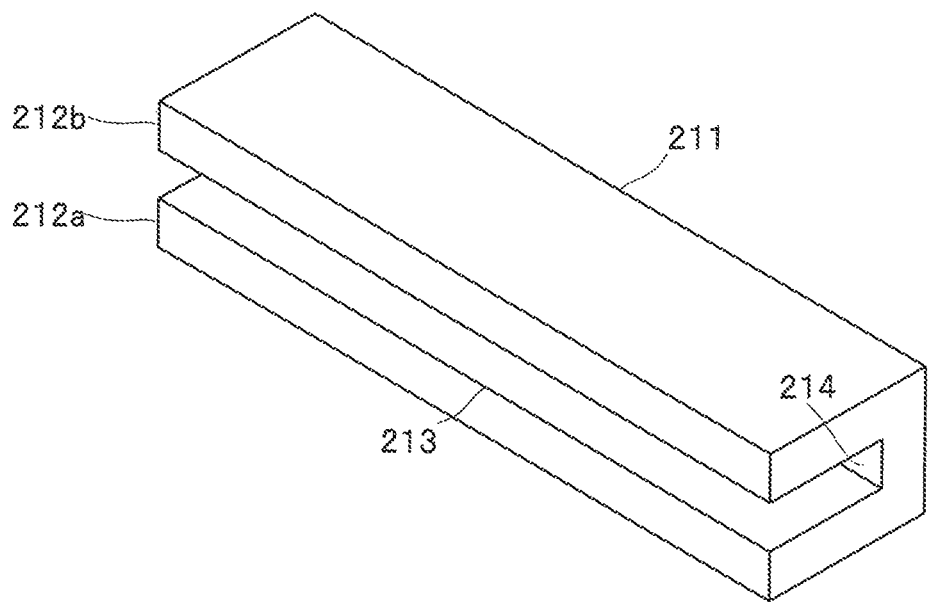
FIG. 9 is a perspective view of a terminal holding member of the endoscope reprocessor according to a modification 1 of the first embodiment of the present invention.
Figure 10:
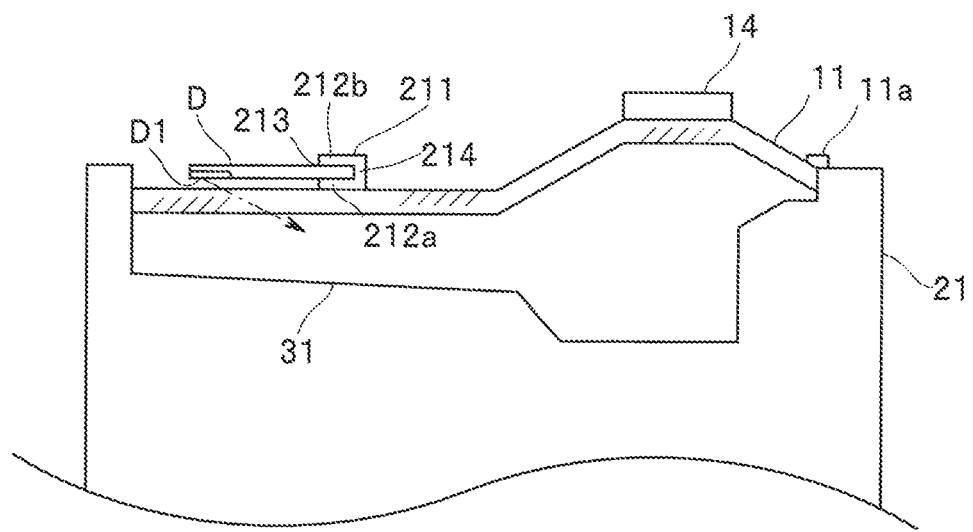
FIG. 10 is an explanatory view for describing a disposition of the terminal holding member of the endoscope reprocessor according to the modification 1 of the first embodiment of the present invention.

FIG. 9 is a perspective view of the terminal holding member 211 of the endoscope reprocessor 1 according to a modification 1 of the first embodiment of the present invention. FIG. 10 is an explanatory view for describing a disposition of the terminal holding member 211 of the endoscope reprocessor 1 according to the modification 1 of the first embodiment of the present invention. In this modification, the description of components substantially identical to the corresponding components in other embodiments and modifications will be omitted. In the same manner, the description of components substantially identical to the corresponding components will be omitted also in other embodiments and modifications described hereinafter.

The terminal holding member 211 is made of a material, such as a resin, ceramic or metal. Assume the case where at least a portion of the terminal holding member sandwiched between the observation terminal D and the top cover 11 is made of a material having visible light transmitting properties and a refractive index identical to a refractive index of the top cover 11. In such a case, it is possible to obtain an advantageous effect that a user can easily observe the display panel of the observation terminal D through the top cover 11.

The terminal holding member 211 is provided to the outer surface of the top cover 11 such that a direction from the other end toward the one end is aligned with a direction in which the observation terminal D is inserted. The terminal holding member 211 includes holding plates 212a, 212b, an insertion opening 213, and an abutment plate 214.

As shown in FIG. 9, the holding plates 212a, 212b are provided substantially parallel to each other in a spaced apart manner by a distance that corresponds to the thickness of the observation terminal D. The lengths and the widths of the holding plates 212a, 212b are determined according to the size of the observation terminal D such that the holding plates 212a, 212b can stably hold the observation terminal D. The holding plate 212a is attached to a front surface of the cover panel 13.

As shown in FIG. 10, the insertion opening 213 is provided on the other end side of the holding plates 212a, 212b. The observation terminal D is inserted into the insertion opening 213 such that the camera D1 faces the treatment tank 31 with the cover panel 13 interposed between the camera D1 and the treatment tank 31.

The abutment plate 214 is continuously formed between the holding plates 212a, 212b on one end side of the holding plates 212a, 212b. The observation terminal D inserted from the insertion opening 213 is caused to abut against the abutment plate 214. When the observation terminal D abuts against the abutment plate 214, the observation terminal D is positioned such that the observation terminal D can pick up an image of the inside of the treatment tank 31. In other words, the terminal holding member 211 has the insertion opening 213 on the other end side of the terminal holding member 211, and include the abutment plate 214 on one end side of the terminal holding member 211, the abutment plate 214 positioning the inserted observation terminal D.

The holding plates 212a, 212b and the abutment plate 214 form a receiving base.

A region surrounded by the holding plates 212a, 212b and the abutment plate 214 form a holding groove.

With such a configuration, the endoscope reprocessor 1 can hold the observation terminal D with the terminal holding member 211 more easily.

Modification 2 of First Embodiment

In the modification 1 of the first embodiment, the holding plate 212b is fixed to the cover panel 13. However, a detachable member 321 may be provided between the holding plate 212b and the cover panel 13.

Figure 11:
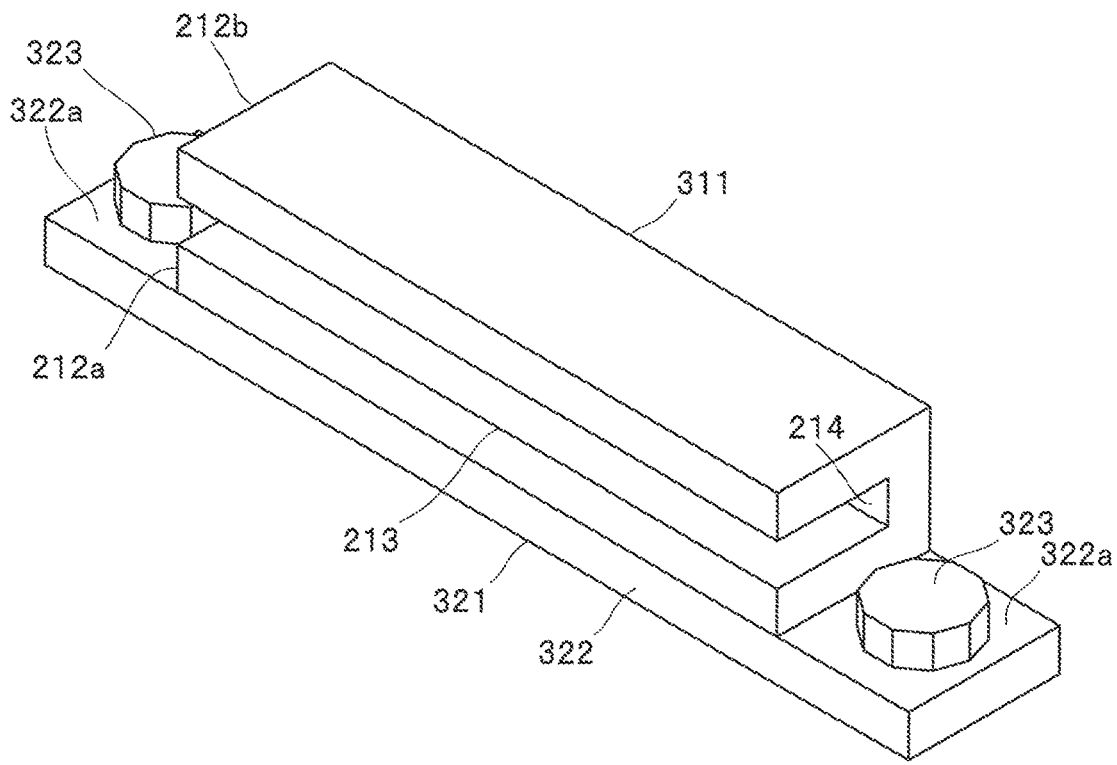
FIG. 11 is an upper perspective view of the terminal holding member of the endoscope reprocessor according to a modification 2 of the first embodiment of the present invention.
Figure 12:
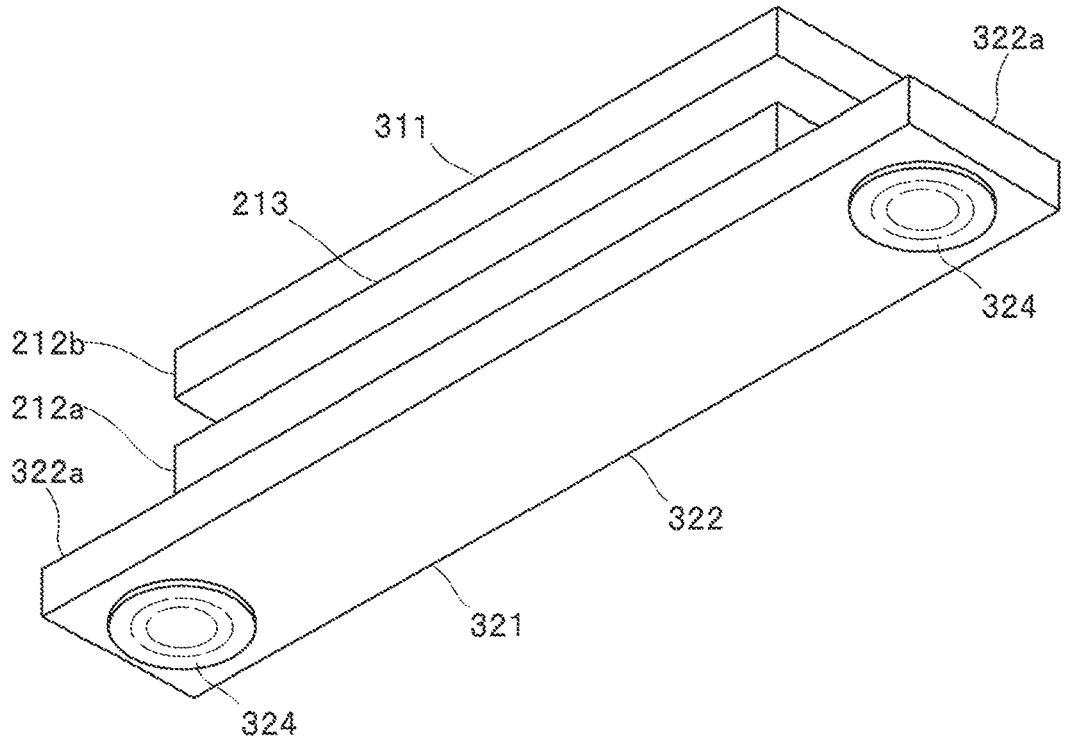
FIG. 12 is a lower perspective view of the terminal holding member of the endoscope reprocessor according to the modification 2 of the first embodiment of the present invention.

FIG. 11 is an upper perspective view of a terminal holding member 311 of the endoscope reprocessor 1 according to a modification 2 of the first embodiment of the present invention. FIG. 12 is a lower perspective view of the terminal holding member 311 of the endoscope reprocessor 1 according to the modification 2 of the first embodiment of the present invention.

The detachable member 321 is detachably attached to the cover panel 13. The detachable member 321 includes a plate body 322, dials 323, and suction cups 324.

The plate body 322 is made of a material, such as a resin or metal. The plate body 322 is continuously formed with the cover panel 13 side of the holding plate 212a. The plate body 322 has a protruding portion 322a at each of both end portions of the plate body 322 in a length direction. The protruding portion 322a protrudes in the length direction from each of both end portions of the holding plate 212a.

The dials 323 are made of a material, such as a resin or metal, and are respectively provided to front surfaces of the protruding portions 322a. Each dial 323 is coupled with the center portion of the suction cup 324 by a screw member provided to penetrate the plate body 322. The dial 323 is turned in a forward direction or a reverse direction by the finger of a user gripping the outer peripheral portion of the dial, thus causing the screw member to advance or retract.

The suction cups 324 are made of a material, such as a resin having elasticity, and are provided to back surfaces of the protruding portions 322a. Each suction cup 324 has a suction surface having a recessed curved shape on a back surface of the suction cup 324, and is detachably attached to the cover panel 13 by a negative pressure.

When the user turns the dial 323 in the forward direction, the screw member pulls the center portion of the suction cup 324 in a direction toward the front surface, so that the suction cup 324 increases a suction force against the cover panel 13. When the user turns the dial 323 in the reverse direction opposite to the forward direction, the screw member pushes back the center portion of the suction cup 324 in a direction toward the back surface, so that the suction cup 324 reduces the suction force against the cover panel 13.

A component to which the terminal holding member 311 is attached is not limited to the top cover 11. The terminal holding member 311 may be detachably attached to another component of the endoscope reprocessor 1.

In other words, the terminal holding member 311 includes the receiving base and the detachable member 321. The receiving base holds the observation terminal D. The detachable member 321 allows the receiving base to be detachably disposed.

With such a configuration, in the endoscope reprocessor 1, the terminal holding member 311 can be detachably attached to the outer surface of the endoscope reprocessor 1 more easily.

Modification 3 of First Embodiment

Assume the case where the observation terminal is held by the terminal holding member such that the display panel of the observation terminal faces the top cover. In such a case, it is preferable to hold the observation terminal at a position where the terminal holding member is prevented from overlapping with the display panel.

With such a configuration, a user can easily observe the display panel of the observation terminal through the top cover.

Figure 13:
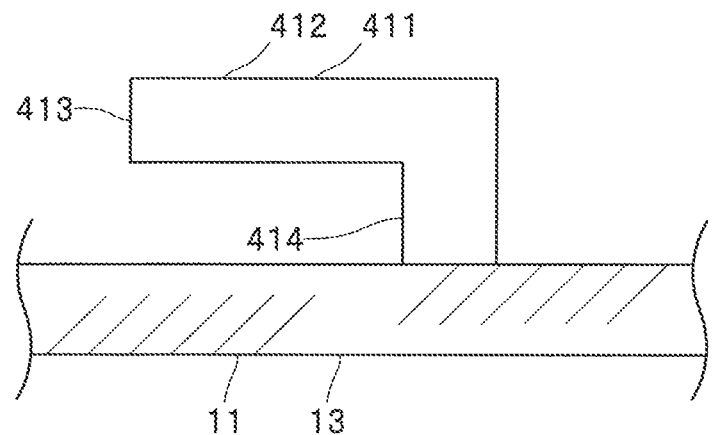
FIG. 13 is a side view of the terminal holding member of the endoscope reprocessor according to a modification 3 of the first embodiment of the present invention.

In the modifications 1 and 2 of the first embodiment, the terminal holding member 211, 311 has a substantially U shape in cross section continuing in the length direction. However, a terminal holding member 411 may have a substantially L shape in cross section continuing in the length direction. In other words, the cover panel 13 or the reprocessor body 21 may play a role of the holding plate 212a in FIG. 9. FIG. 13 is a side view of the terminal holding member 411 of the endoscope reprocessor 1 according to a modification 3 of the first embodiment of the present invention.

The terminal holding member 411 is made of a material, such as a resin, ceramic or metal. The terminal holding member 411 includes a holding plate 412, an insertion opening 413, and an abutment plate 414.

The holding plate 412 is provided substantially parallel to the cover panel 13 in a spaced apart manner by a distance that corresponds to the thickness of the observation terminal D. The length and the width of the holding plate 412 are determined according to the size of the observation terminal D such that the holding plate 412 can stably hold the observation terminal D.

The insertion opening 413 is provided on the other end side of the holding plate 412. The observation terminal D is inserted into the insertion opening 413 such that the camera D1 faces the treatment tank 31 with the cover panel 13 interposed between the camera D1 and the treatment tank 31.

The abutment plate 414 is continuously formed between one end side of the holding plate 412 and the cover panel 13. The observation terminal D inserted from the insertion opening 413 is caused to abut against the abutment plate 414. When the observation terminal D abuts against the abutment plate 414, the observation terminal D is positioned such that the observation terminal D can pick up an image of the inside of the treatment tank 31.

The holding plate 412 and the abutment plate 414 form a receiving base.

A region surrounded by the holding plate 412 and the abutment plate 414 form a holding groove.

A detachable member, such as a suction cup, may be provided between the abutment plate 41 and the cover panel 13, for example.

It may be configured such that the terminal holding member 411 has a substantially rectangular shape in cross section continuing in the length direction, and the terminal holding member 411 and the cover panel 13 form a V shape in cross section. In other words, the holding plate 412 may also serve as the abutment plate 414.

Modification 4 of First Embodiment

In the modification 3 of the first embodiment, the terminal holding member 411 includes no terminal connector 531. However, a terminal holding member 511 may include the terminal connector 531 to which the observation terminal D is connected.

Figure 14:
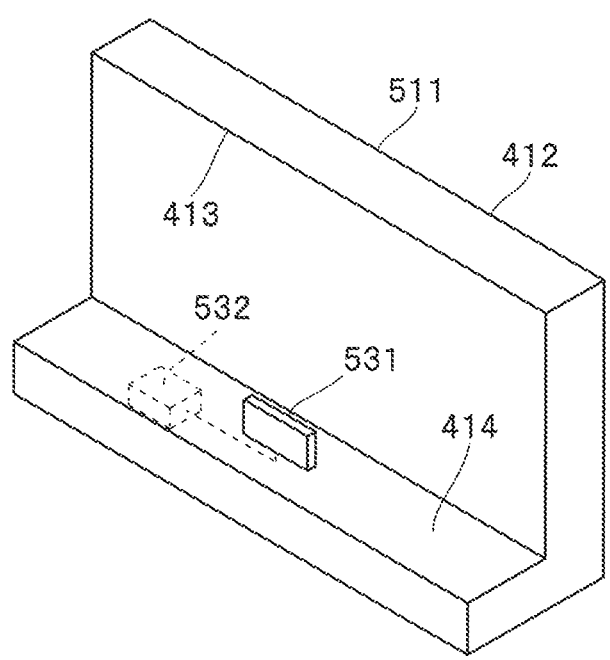
FIG. 14 is a perspective view of the terminal holding member of the endoscope reprocessor according to a modification 4 of the first embodiment of the present invention.

FIG. 14 is a perspective view of the terminal holding member 511 of the endoscope reprocessor 1 according to a modification 4 of the first embodiment of the present invention.

The terminal holding member 511 includes the terminal connector 531 and a battery 532.

The terminal connector 531 is provided on a holding groove side of the abutment plate 414. The terminal connector 531 is configured such that the terminal connector 531 can be connected with the external connection connector D6 of the observation terminal D that is held.

The battery 532 is connected with the terminal connector 531, and outputs power to the observation terminal D connected to the terminal connector 531.

It may be configured such that the terminal connector 531 is connected with an external power source, and outputs power supplied from the external power source to the observation terminal D.

In other words, the terminal holding member 511 includes the insertion opening 413, the abutment plate 414, and the terminal connector 531. The observation terminal D is inserted into the insertion opening 413. The abutment plate 414 positions the inserted observation terminal D. The terminal connector 531 is provided to the abutment plate 414.

With such a configuration, in the endoscope reprocessor 1, power can be supplied to the observation terminal D by the terminal holding member 511.

The terminal connector 531 may be a connector for connecting the observation terminal D with an external memory or other smart device.

Modification 5 of First Embodiment

In the modifications 1 to 4 of the first embodiment, the terminal holding member 211 to 511 holds the observation terminal D substantially parallel to the cover panel 13. However, a terminal holding member 611 may be configured such that the terminal holding member 611 holds the observation terminal D at an angle at which the observation terminal D intersects with the cover panel 13 according to the purpose of use of the observation terminal D.

Figure 15:
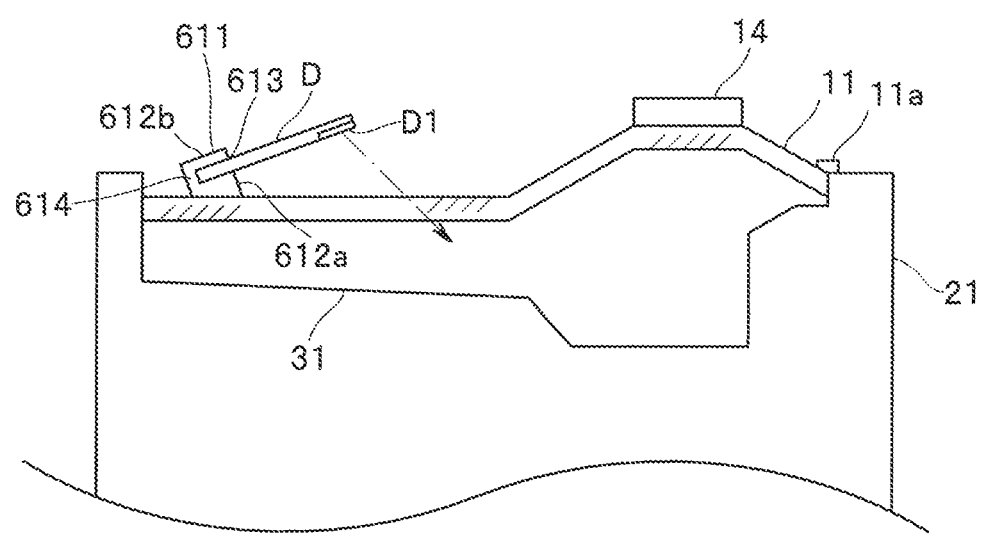
FIG. 15 is an explanatory view for describing a disposition of the terminal holding member of the endoscope reprocessor according to a modification 5 of the first embodiment of the present invention.

FIG. 15 is an explanatory view for describing a disposition of the terminal holding member 611 of the endoscope reprocessor 1 according to a modification 5 of the first embodiment of the present invention.

As shown in FIG. 15, the terminal holding member 611 is made of a material, such as a resin or metal. The terminal holding member 611 is provided to the front surface of the top cover 11 such that a direction from one end toward the other end is aligned with a direction in which the observation terminal D is inserted. The terminal holding member 611 includes holding plates 612a, 612b, an insertion opening 613, and an abutment plate 614.

One surface of the holding plate 612a is provided to the front surface of the cover panel 13. The other surface of the holding plate 612a inclines such that the other surface of the holding plate 612a approaches the top cover 11 as progresses from the one end side toward the other end side. The holding plate 612b is disposed substantially parallel to the holding plate 612a in a spaced apart manner by a distance that corresponds to the thickness of the observation terminal D.

The insertion opening 613 is provided on the one end side of the holding plates 612a, 612b. The observation terminal D is inserted into the insertion opening 613 such that the camera D1, which acts as a receiver, faces the treatment tank 31 with the cover panel 13 interposed between the camera D1 and the treatment tank 31.

The abutment plate 614 is continuously formed between the holding plates 612a, 612b on the other end side of the holding plates 612a, 612b. The observation terminal D inserted from the insertion opening 613 is caused to abut against the abutment plate 614.

The holding plates 612a, 612b and the abutment plate 614 form a receiving base.

A region surrounded by the holding plates 612a, 612b and the abutment plate 614 form a holding groove.

It may be configured such that an inclination angle of the other surface of the holding plate 612a can be adjusted by a user.

With such a configuration, in the endoscope reprocessor 1, the terminal holding member 611 holds the observation terminal D in a state where the observation terminal D is inclined with respect to the treatment tank 31. Therefore, the observation terminal D can pick up a wider field of an image of the treatment tank 31.

Modification 6 of First Embodiment

The observation terminal D may be disposed such that the observation terminal D is prevented from covering a portion of the treatment tank 31 close to one end side.

The terminal holding member 111 is provided to a portion away from the center of the top cover 11. In FIG. 2, the terminal holding member 111 is provided at a portion closer to the other end side than to the center portion, and holds the observation terminal D inserted in a direction from the other end side toward one end side.

With such a configuration, in the endoscope reprocessor 1, a user is allowed to visually check a portion (a dashed-and-double-dotted line in FIG. 2) disposed closer to the one end side than to the center portion of the treatment tank 31. For example, the user is allowed to visually check ejection of liquid from the ejection ports T3 and whether or not liquid is being appropriately discharged from the water supply circulation nozzle 37.

Second Embodiment

In the first embodiment and the modifications 1 to 6 of the first embodiment, the terminal holding member 111 to 611 cannot allow the observation terminal D to rotate with respect to the cover panel 13. However, a terminal holding member 711 may be configured such that the terminal holding member 711 can cause the observation terminal D to be rotated with respect to the cover panel 13.

Figure 16:
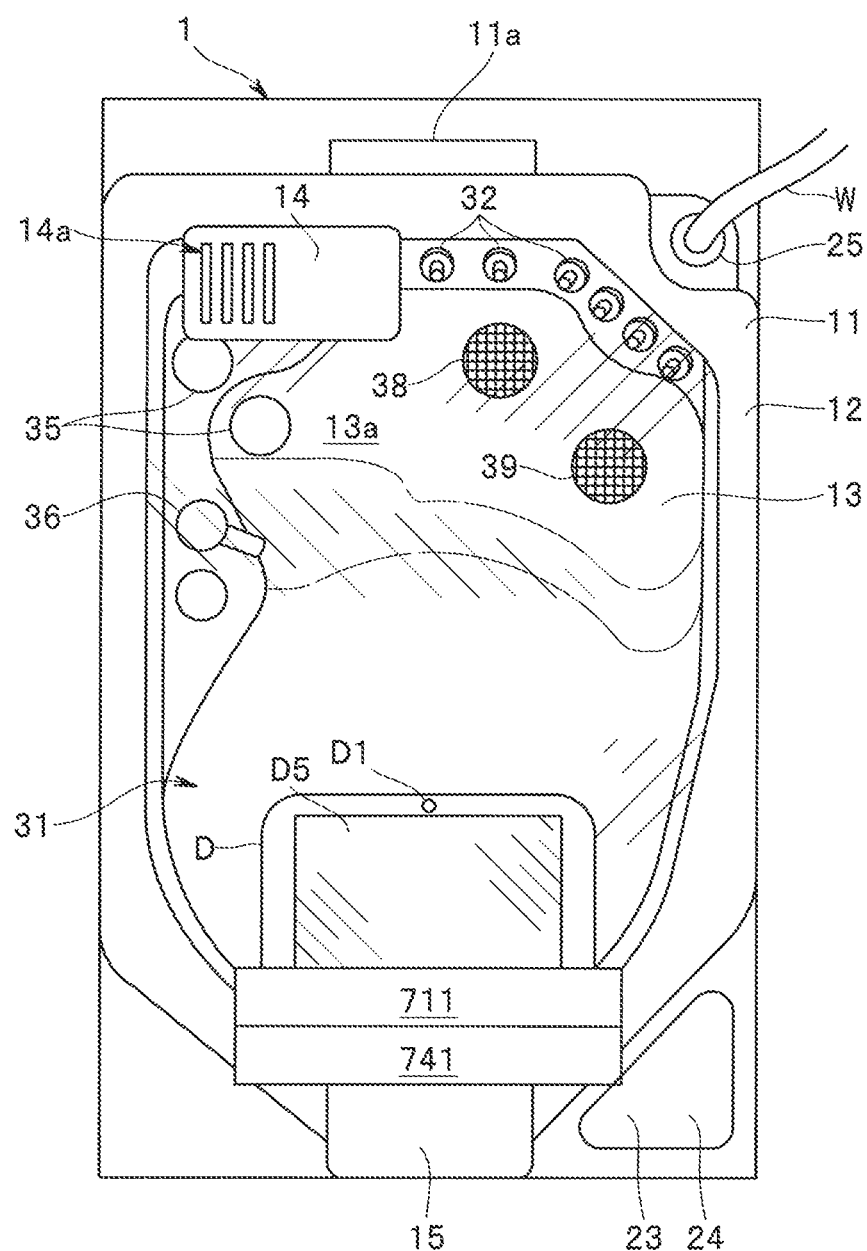
FIG. 16 is a top plan view for describing a first position of a terminal holding member of an endoscope reprocessor according to a second embodiment of the present invention.
Figure 17:
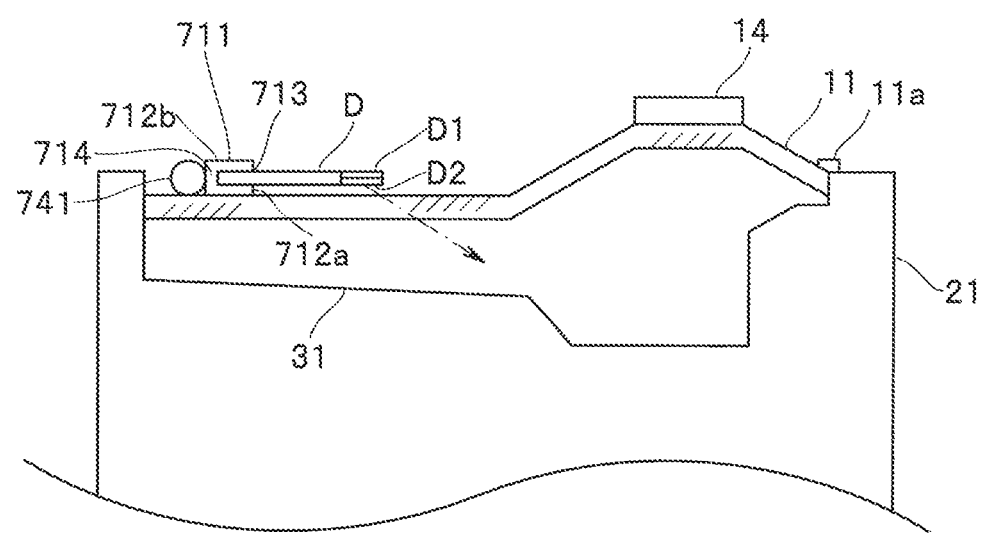
FIG. 17 is an explanatory view for describing the first position of the terminal holding member of the endoscope reprocessor according to the second embodiment of the present invention.
Figure 18:
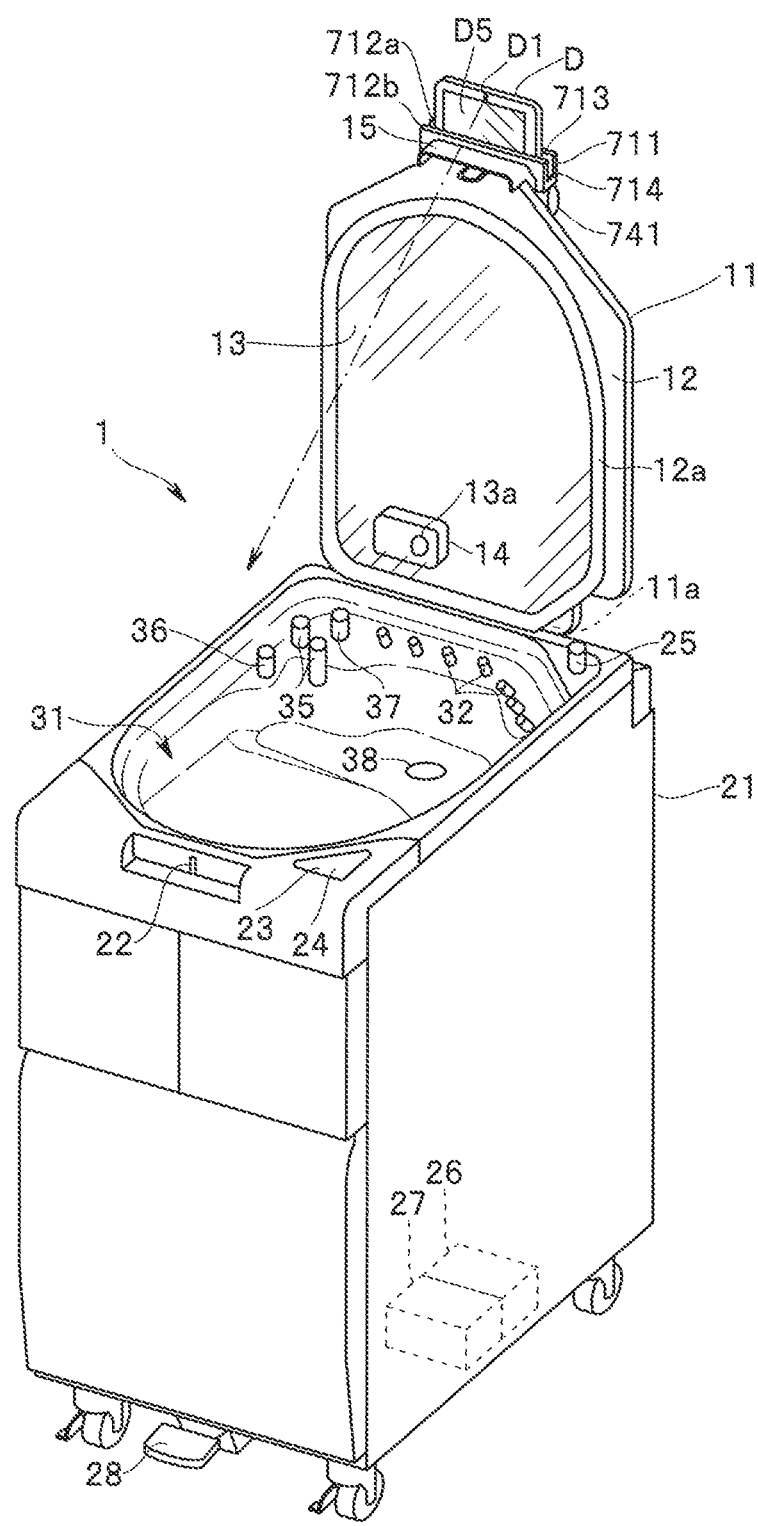
FIG. 18 is a perspective view for describing a second position of the terminal holding member of the endoscope reprocessor according to the second embodiment of the present invention.
Figure 19:
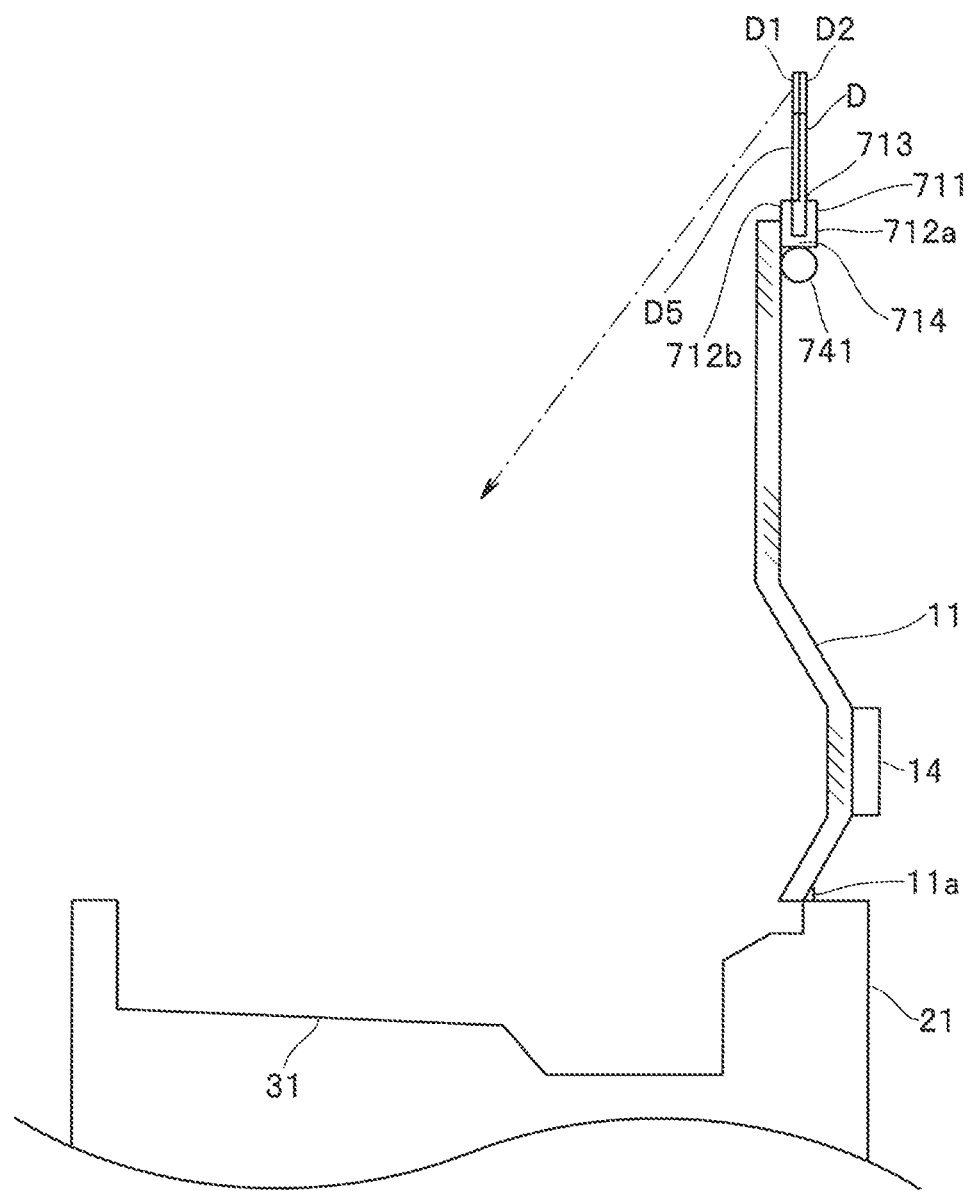
FIG. 19 is an explanatory view for describing the second position of the terminal holding member of the endoscope reprocessor according to the second embodiment of the present invention.

FIG. 16 is a top plan view for describing a first position of the terminal holding member 711 of the endoscope reprocessor 1 according to a second embodiment of the present invention. FIG. 17 is an explanatory view for describing the first position of the terminal holding member 711 of the endoscope reprocessor 1 according to the second embodiment of the present invention. FIG. 18 is a perspective view for describing a second position of the terminal holding member 711 of the endoscope reprocessor 1 according to the second embodiment of the present invention. FIG. 19 is an explanatory view for describing the second position of the terminal holding member 711 of the endoscope reprocessor 1 according to the second embodiment of the present invention.

As shown in FIG. 16 and FIG. 17, the terminal holding member 711 is made of a material, such as a resin or metal. The terminal holding member 711 is provided to the front surface of the top cover 11 such that a direction from one end toward the other end is aligned with a direction in which the observation terminal D is inserted. The terminal holding member 711 includes holding plates 712a, 712b, an insertion opening 713, an abutment plate 714, and a rotating member 741.

The holding plates 712a, 712b are provided substantially parallel to each other in a spaced-apart manner by a distance that corresponds to the thickness of the observation terminal D.

The insertion opening 713 is provided on a side of the holding plates 712a, 712b opposite to the rotating member 741. The observation terminal D is inserted into the insertion opening 713.

The abutment plate 714 is continuously formed between the holding plates 712a, 712b on a rotating member 741 side of the holding plates 712a, 712b.

The observation terminal D is inserted from the insertion opening 713 such that the camera D2 is directed toward the holding plate 712a side, and the camera D1 is directed toward the holding plate 712b side, and the observation terminal D is caused to abut against the observation terminal D.

The holding plates 712a, 712b and the abutment plate 714 form a receiving base.

A region surrounded by the holding plates 712a, 712b and the abutment plate 714 form a holding groove.

The rotating member 741 is provided to the front surface of the top cover 11. The rotating member 741 has a rotation axis extending in a direction orthogonal to a direction in which the observation terminal D is inserted. The rotating member 741 supports the abutment plate 714 such that the abutment plate 714 can rotate about the rotation axis.

With the rotation of the rotating member 741, the terminal holding member 711 is disposed at either one of the first position or the second position.

The first position is a position where the insertion opening 713 is directed to the one end side of the top cover 11. When the terminal holding member 711 is in the first position, the camera D2 is disposed to face the treatment tank 31. When the top cover 11 is brought into the closed state, the terminal holding member 711 is brought into the first position.

As shown in FIG. 18 and FIG. 19, the second position is a position where the insertion opening 713 is directed to the other end side of the top cover 11. When the terminal holding member 711 is in the second position, the camera D1 is disposed to protrude from the other end side of the top cover 11. When the top cover 11 is brought into the open state, the terminal holding member 711 is brought into the second position.

In other words, the terminal holding member 711 includes the receiving base and the rotating member 741. The receiving base holds the observation terminal D. The rotating member 741 rotatably supports the receiving base. The rotating member 741 causes the receiving base to be rotated such that the receiving base is in the first position with the top cover 11 being in the closed state, and the receiving base is in the second position different from the first position with the top cover 11 being in the open state.

With such a configuration, in the endoscope reprocessor 1, it is possible to pick up an image of the inside of the treatment tank 31 in a state where the top cover 11 is brought into the closed state, thus causing the terminal holding member 711 to be brought into the first position.

Further, in the endoscope reprocessor 1, various types of information, such as a manual, an instruction, a notification, or warning, is displayed on the display panel D5 in a state where the top cover 11 is brought into the open state, thus causing the terminal holding member 711 to be brought into the second position. A user can perform a work for reprocessing, such as disposing or connecting the endoscope E in the treatment tank 31 by referencing the various types of information displayed on the display panel D5.

According to the embodiment, the endoscope reprocessor 1 includes the terminal holding member 711 capable of being rotated by the rotating member 741, and can be more easily equipped with the observation terminal D, which determines whether or not the endoscope reprocessor 1 is being used in an appropriate use state.

Third Embodiment

In the first embodiment, the modifications of the first embodiment, and the second embodiment, the endoscope reprocessor 1 has no light reflecting structure. However, the endoscope reprocessor 1 may have the light reflecting structure.

Figure 20:
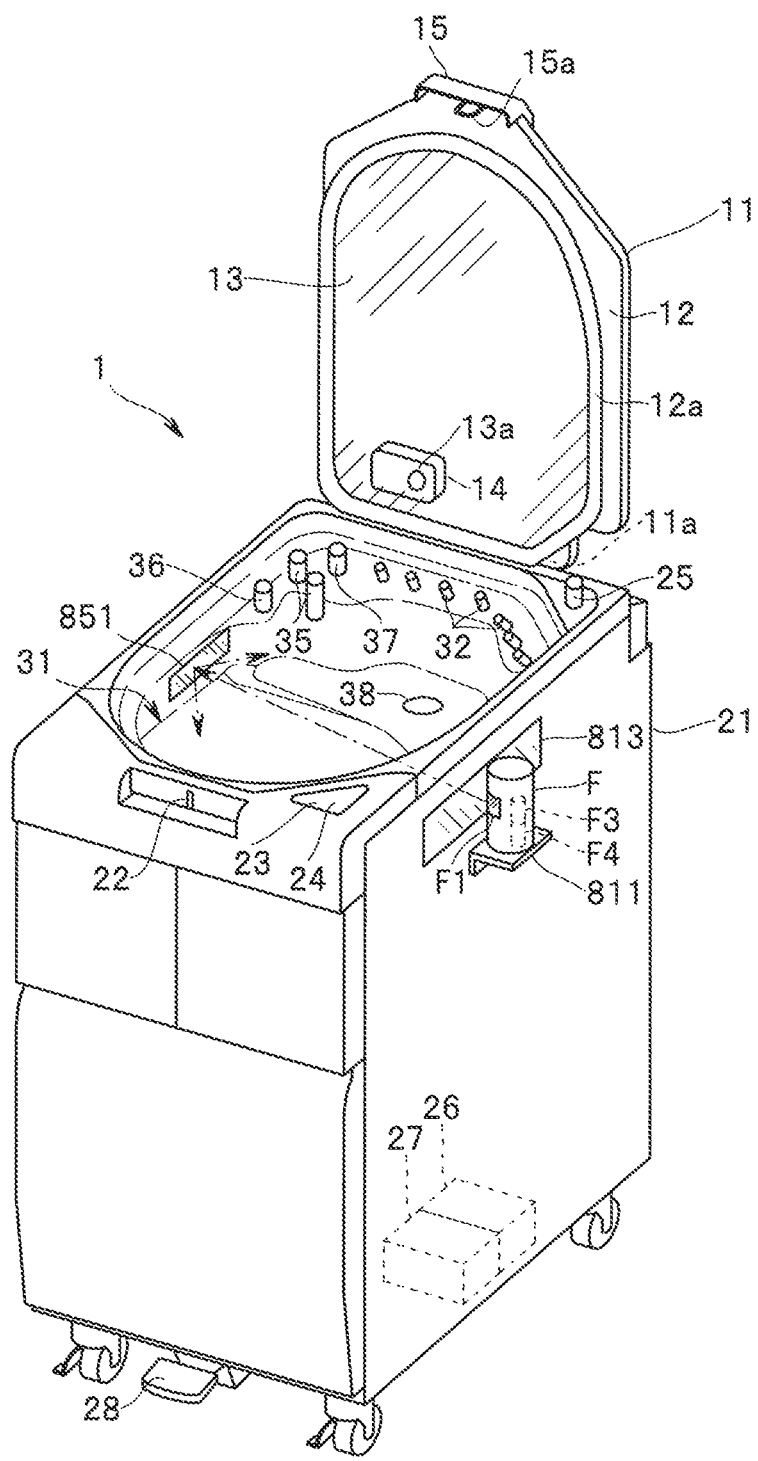
FIG. 20 is a perspective view of an endoscope reprocessor according to a third embodiment of the present invention.

FIG. 20 is a perspective view of the endoscope reprocessor 1 according to a third embodiment of the present invention.

The reprocessor body 21 includes a terminal holding member 811, an observation panel 813, which acts as a transmission panel, a mirror 851 that forms the light reflecting structure, and an observation terminal F.

The terminal holding member 811 is made of a material, such as a resin or metal. The terminal holding member 811 is disposed adjacent to the transmission panel at an outer peripheral side of the reprocessor body 21. The terminal holding member 811 includes a holding base that holds the observation terminal F.

The observation panel 813 is made of a material, such as a resin, and has light transmitting properties. The observation panel 813 is provided to the outer peripheral side of the reprocessor body 21 to allow an observation of the inside of the treatment tank 31.

The mirror 851 is made of a material, such as glass or metal. The mirror 851 is provided to the wall portion of the treatment tank 31 at a position that faces the observation panel 813.

The observation terminal F is held by the terminal holding member 811. The observation terminal F includes a camera F1, a control unit F3, and a communication unit F4.

The camera F1 is disposed such that the camera F1 faces the mirror 851 with the observation panel 813 interposed between the camera F1 and the mirror 851. The camera F1 can pick up an image of the inside of the treatment tank 31 displayed on the mirror 851. The configurations of the control unit F3 and of the communication unit F4 are substantially same as the configurations of the control unit D3 and the communication unit D4 and hence, the repeated description will be omitted.

According to the embodiment, the endoscope reprocessor 1 allows the observation terminal F to observe also the back side of an article accommodated in the treatment tank 31 with the mirror 851, and can be more easily equipped with the observation terminal F, which determines whether or not the endoscope reprocessor 1 is being used in an appropriate use state.

In the embodiments and the modifications, the description has been made for an example where an observation wave is light. However, the observation wave may be an electromagnetic wave including visible light, invisible light, and the like. Further, the observation wave is not limited to an electromagnetic wave, but may be an acoustic wave.

The observation terminal D, F may include a filter that receives only a specific wavelength of the observation wave.

In the embodiments and the modifications, the observation terminal D, F is a portable information terminal of a tablet type or a camera terminal. However, the observation terminal D, F is not limited to the above. The observation terminal D may be a portable information terminal, such as a smartphone, or a camera terminal, such as a Web camera.

In the embodiments and the modifications, one set of the observation terminal D, F and the terminal holding member 111 to 811 is provided. However, the configuration is not limited to such a configuration. A plural sets of the observation terminal D, F and the terminal holding member 111 to 811 may be provided.

In the embodiment and the modifications, the terminal holding member 111 to 811 is configured such that the terminal holding member 111 to 811 can hold a portable information terminal of a tablet type or a camera terminal. However, the shape of the terminal holding member 111 to 811 is not limited to the shape described in the examples in the embodiments and the modifications.

Fourth Embodiment

Unlike the first to third embodiments, in a fourth embodiment, a holding base including the terminal holding member is separate from an endoscope reprocessor.

It is sufficient for the holding base to be able to hold the observation terminal D such that the observation terminal D can observe the treatment tank 31 with the cover panel 13 being in the closed state or in the open state. An example of the shape of the holding base may be a shape of a music stand. Another example of the shape of the holding base may be a shape formed of a hanging portion from which the observation terminal D is hung and a support portion that supports the hanging portion.

The endoscope reprocessor 1, the observation terminal D, or the holding base may include at least one of a detection unit and an informing unit. The detection unit is configured to detect whether or not the treatment tank 31 is within a visual field range of the observation terminal D. The informing unit is configured to inform the detection result from the detection unit.

The endoscope reprocessor 1, the observation terminal D, or the holding base may include at least one of a calculation unit and an informing unit. The calculation unit is configured to calculate a position of the holding base, a height of the holding base, or an angle of the terminal holding member to allow the treatment tank 31 to be within the visual field range of the observation terminal D. The informing unit is configured to inform the calculation result from the calculation unit.

In the embodiments and the modifications, the observation terminal D, F performs determination processing on the detection result. However, a device that performs the determination processing is not limited to the observation terminal D, F. The device that performs the determination processing may be any of a PC terminal, an information terminal such as a server, a portable information terminal such as a smartphone, a wearable device of a type such as a watch type, a pendant type, a brooch type, a glasses type, or a headband hat type, or the reprocessor body 21 instead of the observation terminal D, F.

In the embodiments and the modifications, a notification processing is performed by the reprocessor body 21. However, the configuration is not limited to such a configuration. The notification processing may be performed by any one of a PC terminal, an information terminal such as a server, a portable information terminal such as a smartphone or a tablet, a wearable device of a type such as a watch type, a pendant type, a brooch type, a glasses type, or a headband hat type, a projector, or a virtual image monitor instead of the reprocessor body 21.

The present invention is not limited to the above-mentioned embodiments, and various modifications and applications are conceivable without departing from the gist of the present invention.

What is claimed is:

1. An endoscope reprocessor comprising:
   a treatment tank;
   a top cover including a transmission panel made of a transmitting material that allows an observation wave to transmit through the transmitting material, the transmission panel being disposed such that the observation wave is transmitted from an inside of the treatment tank and through the transmission panel; and
   at least one terminal holding member disposed on an outer surface of the top cover, and the at least one terminal holding member being configured to hold an observation terminal having an image sensor at a position that allows the image sensor to face the transmission panel;
   wherein one end of the top cover is connected to a reprocessor body by a hinge, and another end of the top cover rotates about the one end of the top cover, and
   the terminal holding member is provided such that a direction from the other end toward the one end is aligned with a direction in which the observation terminal is inserted, the terminal holding member having an insertion opening on a side of the other end, and including an abutment plate on a side of the one end, the abutment plate positioning the observation terminal inserted.

2. The endoscope reprocessor according to claim 1, wherein the top cover covers the treatment tank.

3. The endoscope reprocessor according to claim 1, wherein the terminal holding member includes
   a receiving base that holds the observation terminal, and
   a detachable member that allows the receiving base to be detachably disposed.

4. The endoscope reprocessor according to claim 2, wherein the terminal holding member includes
   a receiving base that holds the observation terminal, and
   a rotating member that rotatably supports the receiving base, and
   the rotating member causes the receiving base to be rotated such that
   the receiving base is in a first position with the top cover being in a closed state, and
   the receiving base is in a second position different from the first position with the top cover being in an open state.

5. The endoscope reprocessor according to claim 1, wherein the terminal holding member includes a terminal connector provided to the abutment plate.

6. The endoscope reprocessor according to claim 1, wherein the terminal holding member holds the observation terminal in a state where the observation terminal is inclined with respect to the treatment tank.

7. The endoscope reprocessor according to claim 2, wherein the terminal holding member is provided at a position away from a center of the top cover.

8. The endoscope reprocessor according to claim 2, wherein
   the top cover has a visible light transmitting property, and
   the terminal holding member holds the observation terminal to allow an entire surface of a display panel of the observation terminal to be seen through an inner surface of the top cover in a state where the observation terminal is held by the terminal holding member such that the display panel faces the top cover.

9. The endoscope reprocessor according to claim 8, wherein the terminal holding member includes a first holding member, and a second holding member formed of a portion of the top cover, and the first holding member and the second holding member sandwich the observation terminal to position the observation terminal on the top cover.

10. The endoscope reprocessor according to claim 2, wherein
    the top cover has a visible light transmitting property,
    the terminal holding member holds the observation terminal by clamping the observation terminal, and
    at least a portion of the terminal holding member sandwiched between the observation terminal and the top cover is made of a material having a visible light transmitting property and a refractive index identical to a refractive index of the top cover.

11. An endoscope reprocessor system comprising:
    an endoscope reprocessor, and
    an observation terminal having an image sensor;
    the endoscope reprocessor comprising:
    a treatment tank;
    a top cover including a transmission panel made of a transmitting material that allows an observation wave to transmit through the transmitting material, the transmission panel being disposed such that the observation wave is transmitted from an inside of the treatment tank and through the transmission panel; and at least one terminal holding member disposed on an outer surface of the top cover, and the at least one terminal holding member being configured to hold the observation terminal at a position that allows the image sensor to face the transmission panel;

wherein the observation terminal includes a display for displaying an image captured by the image sensor.

12. The endoscope reprocessor system according to claim 11, wherein the display is provided on a same surface as the image sensor.

13. The endoscope reprocessor system according to claim 11, wherein the image sensor comprises a first image sensor, the observation terminal further comprising a second sensor provided on a second surface of the observation device opposite to a first surface having the first image sensor, and the display is provided on the second surface.

\* \* \* \* \*